United States Patent

Karlsson et al.

[11] Patent Number: 5,753,514
[45] Date of Patent: May 19, 1998

[54] METHOD AND SAMPLE CONTAINER FOR COLLECTING SMALL QUANTITES OF LIQUID SAMPLES

[76] Inventors: Hans Karlsson, Celsiusvagen 4, S-191 44 Sollentuna; Urban Ungerstedt, Mjolnarstigen 11, S-181 46 Lidingo, both of Sweden

[21] Appl. No.: 628,679
[22] PCT Filed: Oct. 7, 1994
[86] PCT No.: PCT/SE94/00940
  § 371 Date: Apr. 10, 1996
  § 102(e) Date: Apr. 10, 1996
[87] PCT Pub. No.: WO95/10357
  PCT Pub. Date: Apr. 20, 1995

[30] Foreign Application Priority Data

Oct. 12, 1993 [SE] Sweden .................... 9303344

[51] Int. Cl.⁶ .................................. G01N 1/10
[52] U.S. Cl. .......................... 436/180; 422/99; 422/100; 422/103; 422/104; 436/174; 436/179; 73/864.11; 73/864.12; 73/864.24
[58] Field of Search .................... 422/99, 100, 102, 422/103, 104; 436/180, 179, 174; 73/864.11, 864.12, 864.24

[56] References Cited

U.S. PATENT DOCUMENTS

| | | | |
|---|---|---|---|
| 4,393,726 | 7/1983 | Tamm et al. | 73/864.84 |
| 4,808,381 | 2/1989 | McGregor et al. | 422/100 |
| 5,163,582 | 11/1992 | Godolphin et al. | 222/1 |
| 5,192,511 | 3/1993 | Roach | 422/100 |
| 5,270,219 | 12/1993 | DeCastro et al. | 436/180 |
| 5,393,674 | 2/1995 | Levine et al. | 436/177 |

FOREIGN PATENT DOCUMENTS 2 807 262  11/1984  Germany.
WO 87/01924  4/1987  WIPO.

*Primary Examiner*—Harold Y. Pyon
*Attorney, Agent, or Firm*—Young & Thompson

[57] ABSTRACT

When small quantities of liquid sample are to be collected from the outlet of a small cannula tube, there is used a sample container (1) which includes a narrow capillary tube (2) whose one end is closed with an elastomeric seal (4) through which the cannula point can be inserted. Instead of taking liquid from the bottom of a vessel, the liquid is permitted to remain unified by means of capillary forces in the capillary tube (2), which forms part of an axial channel. The capillary widens towards the other end, for taking up larger sample quantities.

4 Claims, 1 Drawing Sheet

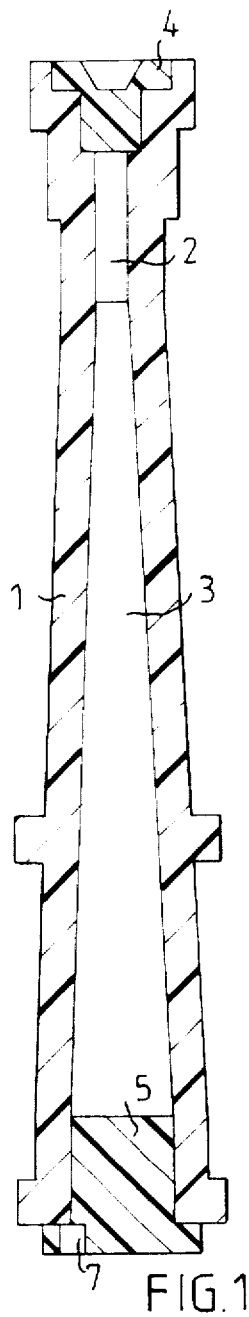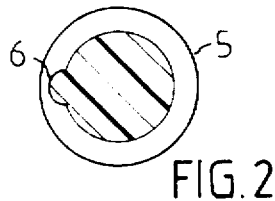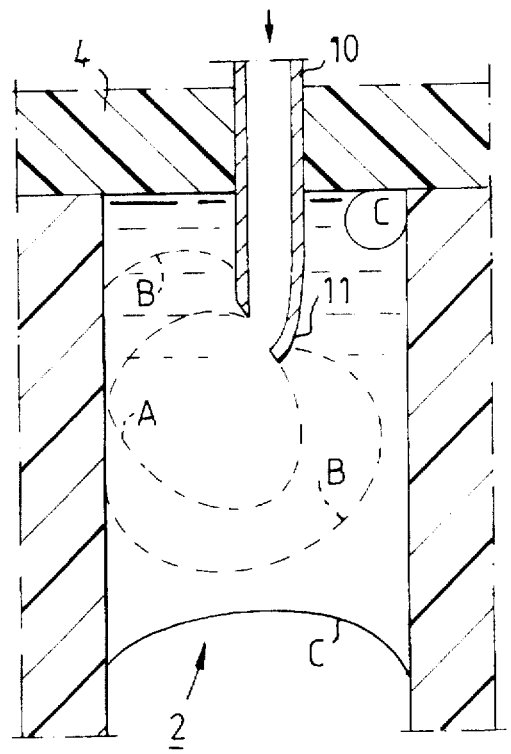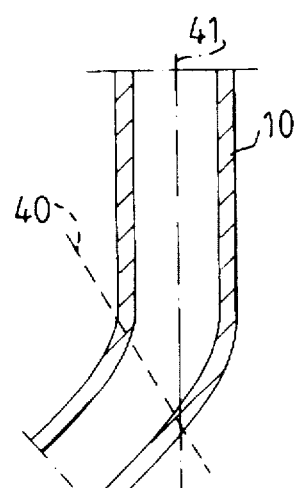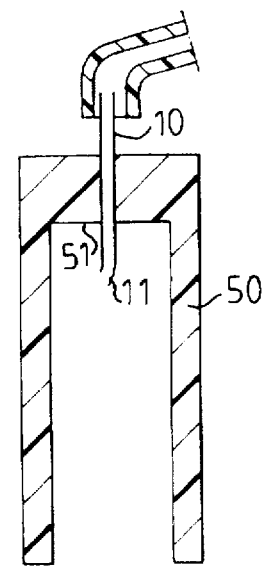

5,753,514

METHOD AND SAMPLE CONTAINER FOR COLLECTING SMALL QUANTITES OF LIQUID SAMPLES

This application is a 371 of PCT/SE94/00940 which filed in Oct. 7, 1994.

FIELD OF THE INVENTION

The present invention relates to a method of collecting and handling small liquid quantities, i.e. liquid quantities which are so small that the surface tension brings about certain difficulties. The invention also relates to a particular design of a sample container and also to a connecting device therefor.

BACKGROUND OF THE INVENTION

The handling of small quantities of liquid samples becomes particularly difficult as soon as one works with volumes at which a droplet (in the case of water, it can be expected that a droplet which falls freely from a narrow tube will be about 15 μl) is not a negligible volume. The handling of such minute volumes presumes that one and the same volume is maintained and that the delivery and withdrawal of such volumes is effected with the aid of hollow tubes (cannula) in contact with the liquid surface. Examples of such handling procedures are described in EP-B-0,223,758, JP-A-55-39029 and JP-A-60-21455. A common factor of this technique is that the samples are collected on and taken from the bottoms of small sample containers with the aid of cannula which is inserted through an opening located opposite the container bottom. The opening is fitted with an elastomeric stopper through which the cannula is inserted and which reseals the hole made by the cannula as the cannula is withdrawn from the stopper.

A primary object of the invention is to provide for improved handling of small or minute sample quantities, primarily liquid samples, both when taking a sample and when later taking quantities of sample for analysis.

SUMMARY OF THE INVENTION

The invention is based on the realization that it is not necessary to work with conventional liquid vessels, i.e. with the liquid on a bottom, when dealing with such minute volumes. The main aim is to be able to work with maintained volumes that can be repeatedly delivered to and withdrawn from a known position. The surface tension is one of the factors that contributes thereto, as with the known technique. However, according to the starting point of the present invention, the liquid shall be contained in a tubular part of a sample container, this tubular part having a small diameter and being located close to a cannula inlet, preferably in the upper part of the container. The sample container can be handled in any desired position in relation to the vertical, and can even be handled with the container standing upright with the liquid in the upper part of the container. However, in view of the fact that the effect of gravity on such small droplets will be small in relation to the capillary force, the sample container may be positioned in any direction whatsoever in relation to vertical.

To enable slightly larger quantities to be handled, the sample container can be widened in the extension of a narrow, substantially cylindrical part at the mouth or orifice of the container, for instance widened conically. In this case, much larger quantities of liquid can be retained in a unified state in the widened part of the container, through the medium of its cylindrical part. The elongated part of the container at the orifice-end thereof will preferably have a diameter which is not greater than about 3 mm, although the diameter may be smaller as required and as is possible.

One particular advantage gained by allowing the small quantity of liquid to be held in a capillary which lies close to the inlet opening that is closed by an elastomeric stopper is that the liquid will present significant stability against impact forces from a purely mechanical aspect, and it is often possible to avoid the liquid being spread into the sample container and therewith difficult to recollect should the tube be dropped.

It is suitable to provide a small leakage facility, especially at the opposite end of the sample container, with the intention of achieving pressure equalization. According to one preferred embodiment of the invention, this is achieved by fitting in the opposite end an elastomeric stopper which is provided with an axially extending bead, so as to prevent the stopper effectively sealing the container at this end. In this case, an additional seal is fitted in the case of long-term storage or transportation of the container. However, this leakage facility, or air vent, is unnecessary when a sample container is intended exclusively for very minute volumes, when only the total volume of the container is large in relation to the sample volume.

In certain cases, there is a danger of a sample volume being changed by the evaporation of volatile products. In this case, according to one particular embodiment of the invention, the sample capillary may initially be filled either completely or partially with an inert liquid, such as silicone oil, which, when present, will sealingly embrace the sample. According to another embodiment, some form of membrane may be provided in the end of the tube opposite to the inlet end, this membrane presenting only slight resistance. An example in this respect is a hollow stopper provided with a thin wall, similar to the configuration of a finger stall, which sealingly lies against the inner wall but which is comprised solely of a thin wall at the end facing towards the inlet end.

Delivery of a microsample is effected by inserting a pointed needle through the elastomeric stopper, such as an injection-type needle, to a distance on the inward side of the stopper that is small in relation to the length of the anticipated liquid column. Because liquid introduced into the tube at a point which lies very close to the stopper, it is possible to avoid the formation of a bubble, or at least to avoid any such bubble becoming large. Thus, the microsample will preferably be introduced into the tube at a distance from the stopper that does not exceed the diameter of the elongated space.

When withdrawing liquid from the container, it is often suitable to insert the needle a little further into the aforesaid space, particularly when not all of the sample volume present is to be withdrawn. This is because it is not always possible to avoid the formation of a small bubble when introducing the sample into the container, and because any such bubble that may be present can be by-passed by the collecting cannula. When the liquid sample is introduced into the container through the medium of an air-filled tube, it is difficult to avoid the formation of a small air bubble, at least at times. If, as in special circumstances, a small quantity of inert liquid is placed initially in the tube end, a bubble of this liquid may easily land adjacent the elastomeric stopper even then.

In order to obtain a correct penetration length, it is suitable to provide the cannula with a holder or a fender which will prevent penetration of the cannula beyond this point as the cannula is inserted. This is a practical expedient, particularly when taking samples.

It has been found that when using conventional needles where the point is formed by grinding a cannular tube to an angle, the needle point is liable to act as a hollow spout and cut a more or less cylindrical plug from the elastomeric stopper, wherewith the plug may block the cannula and will at least create all kinds of problems, such as deficient sealing in the elastomeric wall when the cannula is withdrawn. To eliminate this, it is proposed that the cannula is curved to a radius in the vicinity of its point before grinding, in principle so that the grinding plane will intersect the tangent to the largest outer radius approximately at a point which lies centrally on the non-curved centre axis of the cannula. This will avoid the aforesaid hollow-spout effect.

BRIEF DESCRIPTION OF THE DRAWINGS

The invention will now be described in more detail with reference to a non-limiting exemplifying embodiment thereof and also with reference to the accompanying drawings.

FIG. 1 is a sectional view of a test tube. FIG. 2 is a sectional view of a stopper which is intended to be fitted into the large end of a test tube. FIG. 3 is a schematic enlarged cross-sectional view of the narrow end of a test tube and shows filling of the test tube with liquid from the point of a cannula. FIG. 4 is an enlarged view of a cannula point. FIG. 5 is a sectional view of a connecting device.

DETAILED DESCRIPTION OF THE INVENTION

FIG. 1 is a sectional view of one example of a test tube for use in accordance with the invention, the illustrated test tube being shown four times its proper size and according to scale. In the illustrated case, the tube 1 is rotationally symmetrical and is die-cast in uncoloured or plain polystyrene. The test tube cavity includes a narrow cylindrical part 2 and a widening conical part 3 which merges with the cylindrical part 2. Elastomeric stoppers, in the illustrated case made from "Santopren 64" are inserted into the ends of the test tube. The stopper 4 inserted into the small end of the test tube seals this end of the tube and is intended to be pierced by the point of a cannula for the purpose of introducing or withdrawing liquid sample substance into and out of the tube respectively. FIG. 2 is a radial cross-section of the stopper 5 and shows the stopper removed from the tube, and it will be seen that the part intended for insertion into the large end of the tube 1 has an axially extending bead such that when the stopper is inserted, its cross-section close to the bead will be deformed so as to form narrow gaps between the tube wall and the stopper proximal to the bead 6. As shown in FIG. 1, the outermost end of the stopper 5, which is not primarily intended to be pierced by the needle, is provided with an opening 7. This will result in a microleakage which will eliminate any differences in pressure that are generated when liquid sample is introduced into or withdrawn from the inner space of the tube. As before mentioned, this equalization of pressure may alternatively be achieved with some form of membrane closure instead of a microleakage facility, which would also afford better protection against the evaporation of volatile substances in particular. In the case of long-term storage or cold storage, this end of the test tube or even both ends of the test tube may be provided with further seals. To this end, the ends of the test tube will suitably be provided with external lips, as shown in FIG. 1, wherein the lip dimensions correspond to standard measurements of crimpable aluminum closures with a membrane placed freely at the centre.

The choice of material will depend on the intended use. In the case of water-based samples, the material will preferably be slightly hydrophobic. In the majority of cases, the aforesaid plastic material will be satisfactory and is also beneficial from the aspect of manufacture. When the sample contains dissolved gases, it is necessary to use a gas-impervious material. In special cases, surface adsorption and absorption may also create problems that may require a particular material to be chosen, both with regard to the tube material and to the choice of the elastomeric material used.

In the illustrated case, the tube has a total length of 38.5 mm. The internal diameter of the narrowest part is 1.1 mm and the length of the narrow part is about 5 mm, meaning that the cylindrical part is able to accommodate about 5 µl. A much larger volume can be accommodated when also using the conical part of the space.

FIG. 3 illustrates very schematically part of a cross-section through the upper part of the cylindrical capillary part 2 and the stopper 4. The stopper 4 is shown to be pierced by a cannular tube 10 having a point 11. When introducing liquid into the capillary part, the liquid will initially hang like a sack formed by surface tension and as the sack increases in size it will begin to wet the inner surface of said part, roughly in the manner of the small droplet A shown in broken lines. This droplet will gradually swell to the full inner diameter of the tube while passing through the configuration B shown in broken lines. When the full diameter of the tube has been filled, it is highly likely that a small air bubble will remain in the upper corner, as illustrated. Should such a bubble form, the bubble will normally be spherical and taken-up in an imaginary cake slice at a 10° angle. Accordingly, the cannula will preferably be inserted to a greater depth when taking liquid from the test tube than when introducing liquid thereinto.

When inserting the cannula through the elastomeric stopper 4 (FIG. 1), the obliquely ground point of the cannular tube is liable to function as a hollow spout and cut a small plug from the stopper, which initially will be seated in the cannula orifice but which is liable to be pressed out by the liquid as the liquid passes through the cannula. This renders handling unsafe, or uncertain, partly because the speed at which the liquid is introduced can suddenly increase when the plug loosens, and partly because the small plug may fall into the sample, from where it can be picked up by another cannula used to withdraw liquid, and subsequently block the system. Furthermore, the plug that has been cut from the stopper will leave behind a hole which prevents the tube from being effectively sealed when the cannula is withdrawn. Furthermore, such a cannula will not pass straight through the stopper, but will tend to bend as it is inserted.

In order to avoid these problems, it is preferred to use a cannula whose first cutting point does not lie in the extension of the cylindrical mantle surface of the cannula but instead lies close to the extension of its centre axis. Such a point is obtained by bending the cannula tube to a radius, preferably over a mandrill. The tube is then ground along a plane 40, see FIG. 4, so that the plane 40 will intersect the downwardly-outwardly turned part of the mantle surface at a point which corresponds approximately to the symmetry axis 41 of the essential length of the tube. As a needle point of this configuration is pressed into an elastomeric stopper in a test tube, the elastomer will endeavour to separate in opposite directions in relation to the needle point and the elastomer application surface will be bent towards the point from both directions, wherewith the ground surface of the needle at its part distal from the point will not wish to cut through the elastomer but rather press the elastomer to one side. The hole formed by this piercing action will reclose readily when the cannula is withdrawn.

FIG. 5 is a sectional view of one example of a connecting device for use together with the test tube shown in FIG. 1. In this case, the connecting device 50 is comprised of a tube into which the test tube can be inserted and which has a bottom 51 from which a needle point 11 projects. The cannula tube is connected externally of the device 50 to a plastic hose for instance, this hose being connected to a sample source which may, for instance, be the outgoing tube of a microdialysis probe inserted into the tissue of a patient. If the tube 50 is so short that the large end of the test tube will project out from the tube when the test tube is pierced and connected to the cannula, it is extremely simple to replace the test tube, a feature which is of particular value when wishing to take successive samples in different contexts. In the case of periodic sampling, unqualified personnel can be entrusted to change the test tubes after having been given brief instructions in this regard.

An inventive sample holder may also be used in many instances together with known devices for taking a sample from the bottom of a test tube. The sample is then taken in accordance with known techniques, by inserting a cannula through the opening in the large end of a sample holder. The position of the sample quantity is, after all, particularly well defined.

The invention can be applied in many contexts. It has already been mentioned that the invention can be applied in human medical contexts. However, the invention can also be applied in animal testing, in growth physiology, when studying maturing processes in the foodstuff industry, and so on.

A device corresponding to the device shown in FIG. 5 may also be used when a sample that has been taken shall later be analyzed, wherein the needle point 11 will preferably be inserted to a greater distance from the bottom wall, as already mentioned.

We claim:

1. In a method for collecting and handling small quantities of liquid sample, which comprises introducing liquid into and withdrawing liquid from a sample container with a cannula tube having a pointed end which is inserted through an elastomeric seal fitted into an orifice at one end of the sample container, the improvement wherein the sample container includes adjacent said orifice an end wall which delimits an elongated space having a diameter of at most 3 mm, which lies adjacent the elastomeric seal; and when liquid is introduced into the container, inserting the pointed end of the cannula tube through the elastomeric seal to an inward location thereof such that the opening of the pointed end will lie in close proximity to the seal, so as to ensure that the liquid introduced will remain unified by capillary forces in the container and to avoid the occurrence of a bubble when introducing liquid to the container, and to minimize the size of such a bubble should it occur, and wherein when liquid is withdrawn from the sample container with the cannula tube inserted therein, the pointed end of the cannula tube is inserted to a further extent than when liquid is introduced into the tube, so as to prevent withdrawal of any bubble that may have formed.

2. A method according to claim 1, further comprising piercing the elastomeric seal with a cannula having a central axis, and whose pointed end is located close to the central axis.

3. A method according to claim 1, wherein the sample container has a through-passing axial passage whose end that lies distal from the elastomeric seal is closed by means of a stopper which includes a leakage facility.

4. A method according to claim 1, wherein the sample container distal from the elastomeric seal is provided with a resilient seal.

* * * * *